(12) United States Patent
Sales et al.

(10) Patent No.: US 10,542,915 B2
(45) Date of Patent: *Jan. 28, 2020

(54) SYSTEMS, APPARATUS, AND METHODS FOR USING A WEARABLE DEVICE TO CONFIRM THE IDENTITY OF AN INDIVIDUAL

(71) Applicant: Vision Service Plan, Rancho Cordova, CA (US)

(72) Inventors: Jay William Sales, Sacramento, CA (US); Richard Chester Klosinski, Jr., Sacramento, CA (US); Matthew Allen Workman, Sacramento, CA (US); Meghan Kathleen Murphy, Davis, CA (US); Matthew David Steen, Sacramento, CA (US)

(73) Assignee: Vision Service Plan, Rancho Cordova, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/259,646

(22) Filed: Jan. 28, 2019

(65) Prior Publication Data
US 2019/0159700 A1     May 30, 2019

Related U.S. Application Data

(60) Continuation of application No. 15/594,898, filed on May 15, 2017, now Pat. No. 10,188,323, which is a
(Continued)

(51) Int. Cl.
*G02C 1/00* (2006.01)
*A61B 5/11* (2006.01)
(Continued)

(52) U.S. Cl.
CPC .............. *A61B 5/112* (2013.01); *A61B 3/112* (2013.01); *A61B 5/0002* (2013.01);
(Continued)

(58) Field of Classification Search
CPC ...... A61B 5/0022; A61B 5/1116; G02C 11/10
(Continued)

(56) References Cited

U.S. PATENT DOCUMENTS 3,505,879 A     4/1970  Vanderberg
3,548,663 A    12/1970  Radin
(Continued)

FOREIGN PATENT DOCUMENTS

EP     2778612     12/2017
GB     2396421     6/2004
(Continued)

OTHER PUBLICATIONS

Final Office Action, dated Dec. 11, 2018, from corresponding U.S. Appl. No. 14/610,501.
(Continued)

*Primary Examiner* — Hung X Dang
(74) *Attorney, Agent, or Firm* — Brient IP Law, LLC

(57) ABSTRACT

A wearable device includes at least one sensor for obtaining a unique identifier from the wearer when the wearer and for transmitting the unique identifier to one or more computer processors for use in determining whether the wearer is a particular individual. The wearable device may also include a wireless communications device for transmitting a signal (e.g., to a remote computing device) that confirms the identity of the wearer as the particular individual. A remote computing device, or other device, or individual, may then, based at least in part on receiving the signal, grant wearer access to a computer program, computing system, and/or a particular physical space.

20 Claims, 4 Drawing Sheets

Related U.S. Application Data division of application No. 14/588,122, filed on Dec. 31, 2014, now Pat. No. 9,649,052.

(60) Provisional application No. 62/046,406, filed on Sep. 5, 2014.

(51) Int. Cl.

| | | |
|---|---|---|
| *A61B 5/00* | (2006.01) | |
| *G06F 19/00* | (2018.01) | |
| *G06K 9/00* | (2006.01) | |
| *G16H 40/63* | (2018.01) | |
| *G16H 50/20* | (2018.01) | |
| *A61B 5/117* | (2016.01) | |
| *A61B 3/11* | (2006.01) | |
| *A61B 5/0402* | (2006.01) | |
| *A61B 5/0476* | (2006.01) | |
| *A61B 5/103* | (2006.01) | |
| *A61B 5/1171* | (2016.01) | |
| *A61B 5/16* | (2006.01) | |
| *A61B 7/04* | (2006.01) | |
| *G09B 5/00* | (2006.01) | |
| *A61B 5/1455* | (2006.01) | |
| *G06K 9/62* | (2006.01) | |
| *G08B 21/04* | (2006.01) | |
| *A63B 24/00* | (2006.01) | |
| *G09B 5/06* | (2006.01) | |
| *G09B 19/00* | (2006.01) | |
| *G06F 21/35* | (2013.01) | |
| *G07C 9/00* | (2006.01) | |
| *G08B 21/02* | (2006.01) | |
| *H04L 29/06* | (2006.01) | |
| *G16H 20/40* | (2018.01) | |
| *A61F 2/76* | (2006.01) | |
| *A61B 5/0205* | (2006.01) | |
| *A61B 5/024* | (2006.01) | |
| *A61B 5/053* | (2006.01) | |
| *A61B 5/08* | (2006.01) | |
| *G02C 11/00* | (2006.01) | |

(52) U.S. Cl.
CPC .......... *A61B 5/0022* (2013.01); *A61B 5/0077* (2013.01); *A61B 5/0402* (2013.01); *A61B 5/0476* (2013.01); *A61B 5/1032* (2013.01); *A61B 5/1103* (2013.01); *A61B 5/117* (2013.01); *A61B 5/1114* (2013.01); *A61B 5/1116* (2013.01); *A61B 5/1128* (2013.01); *A61B 5/1176* (2013.01); *A61B 5/14552* (2013.01); *A61B 5/165* (2013.01); *A61B 5/4076* (2013.01); *A61B 5/4266* (2013.01); *A61B 5/443* (2013.01); *A61B 5/486* (2013.01); *A61B 5/4884* (2013.01); *A61B 5/6803* (2013.01); *A61B 5/7246* (2013.01); *A61B 5/7278* (2013.01); *A61B 7/04* (2013.01); *A63B 24/0062* (2013.01); *G06F 19/00* (2013.01); *G06F 19/3481* (2013.01); *G06F 21/35* (2013.01); *G06K 9/00348* (2013.01); *G06K 9/00597* (2013.01); *G06K 9/00604* (2013.01); *G06K 9/00617* (2013.01); *G06K 9/00664* (2013.01); *G06K 9/6201* (2013.01); *G07C 9/00158* (2013.01); *G08B 21/02* (2013.01); *G08B 21/0423* (2013.01); *G08B 21/0461* (2013.01); *G08B 21/0476* (2013.01); *G09B 5/00* (2013.01); *G09B 5/06* (2013.01); *G09B 19/0092* (2013.01); *G16H 20/40* (2018.01); *G16H 40/63* (2018.01); *G16H 50/20* (2018.01); *H04L 63/0861* (2013.01); *A61B 5/024* (2013.01); *A61B 5/0205* (2013.01); *A61B 5/0531* (2013.01); *A61B 5/0816* (2013.01); *A61B 5/1118* (2013.01); *A61B 5/7282* (2013.01); *A61B 2560/0475* (2013.01); *A61B 2562/0219* (2013.01); *A61B 2562/0223* (2013.01); *A61B 2562/0257* (2013.01); *A61B 2576/00* (2013.01); *A61F 2/76* (2013.01); *A61F 2002/7695* (2013.01); *G02C 11/10* (2013.01)

(58) Field of Classification Search
USPC .................................................. 351/158, 41
See application file for complete search history.

(56) References Cited

U.S. PATENT DOCUMENTS

| | | |
|---|---|---|
| 3,972,038 A | 7/1976 | Fletcher et al. |
| 4,100,401 A | 7/1978 | Tutt et al. |
| 4,186,609 A | 2/1980 | Baermann |
| 4,195,642 A | 4/1980 | Price et al. |
| 4,281,663 A | 8/1981 | Pringle |
| 4,407,295 A | 10/1983 | Steuer et al. |
| 4,434,801 A | 3/1984 | Jiminez et al. |
| 4,855,942 A | 8/1989 | Bianco |
| 4,878,749 A | 11/1989 | McGee |
| 4,919,530 A | 4/1990 | Hyman |
| 5,422,816 A | 6/1995 | Sprague et al. |
| 5,452,480 A | 9/1995 | Ryden |
| 5,497,143 A | 3/1996 | Matsuo et al. |
| 5,585,871 A | 12/1996 | Linden |
| 5,670,872 A | 9/1997 | Van De Walle et al. |
| 5,746,501 A | 5/1998 | Chien et al. |
| 5,891,042 A | 4/1999 | Sham et al. |
| 5,931,764 A | 8/1999 | Freeman et al. |
| 5,966,680 A | 10/1999 | Butnaru |
| 5,976,083 A | 11/1999 | Richardson et al. |
| 6,013,007 A | 1/2000 | Root et al. |
| 6,183,425 B1 | 2/2001 | Whalen et al. |
| 6,218,958 B1 | 4/2001 | Eichstaedt et al. |
| 6,241,684 B1 | 6/2001 | Amano et al. |
| 6,325,507 B1 | 12/2001 | Jannard et al. |
| 6,381,482 B1 | 4/2002 | Jayaraman et al. |
| 6,431,705 B1 | 8/2002 | Linden |
| 6,439,067 B1 | 8/2002 | Goldman et al. |
| 6,513,532 B2 | 2/2003 | Mault et al. |
| 6,532,298 B1 | 3/2003 | Cambier et al. |
| 6,736,759 B1 | 5/2004 | Stubbs et al. |
| 6,769,767 B2 | 8/2004 | Swab et al. |
| 6,783,501 B2 | 8/2004 | Takahashi et al. |
| 6,790,178 B1 | 9/2004 | Mault et al. |
| 6,812,845 B2 | 11/2004 | Yuzuki et al. |
| 7,181,345 B2 | 2/2007 | Rosenfeld et al. |
| 7,187,960 B2 | 3/2007 | Abreu |
| 7,192,136 B2 | 3/2007 | Howell et al. |
| 7,255,437 B2 | 8/2007 | Howell et al. |
| 7,376,238 B1 | 5/2008 | Rivas et al. |
| 7,380,936 B2 | 6/2008 | Howell et al. |
| 7,400,257 B2 | 7/2008 | Rivas |
| 7,401,918 B2 | 7/2008 | Howell et al. |
| 7,438,410 B1 | 10/2008 | Howell et al. |
| 7,454,002 B1 | 11/2008 | Gardner et al. |
| 7,457,434 B2 | 11/2008 | Azar |
| 7,481,531 B2 | 1/2009 | Howell et al. |
| 7,488,294 B2 | 2/2009 | Torch |
| 7,500,746 B1 | 3/2009 | Howell et al. |
| 7,500,747 B2 | 3/2009 | Howell et al. |
| 7,515,054 B2 | 4/2009 | Torch |
| 7,543,934 B2 | 6/2009 | Howell et al. |
| 7,581,833 B2 | 9/2009 | Howell et al. |
| 7,621,634 B2 | 11/2009 | Howell et al. |
| 7,630,524 B2 | 12/2009 | Lauper et al. |
| 7,634,379 B2 | 12/2009 | Noble |
| 7,640,135 B2 | 12/2009 | Vock et al. |
| 7,648,463 B1 | 1/2010 | Elhag et al. |

(56) References Cited

U.S. PATENT DOCUMENTS

| | | |
|---|---|---|
| 7,677,723 B2 | 3/2010 | Howell et al. |
| 7,771,046 B2 | 8/2010 | Howell et al. |
| 7,792,552 B2 | 9/2010 | Thomas et al. |
| 7,793,361 B2 | 9/2010 | Ishihara et al. |
| 7,857,772 B2 | 9/2010 | Bouvier et al. |
| 7,806,525 B2 | 10/2010 | Howell et al. |
| 7,922,321 B2 | 4/2011 | Howell et al. |
| 7,987,070 B2 | 7/2011 | Kahn et al. |
| 8,007,450 B2 | 8/2011 | Williams |
| 8,011,242 B2 | 9/2011 | O'Neill et al. |
| 8,081,082 B2 | 12/2011 | Malik et al. |
| 8,109,629 B2 | 2/2012 | Howell et al. |
| 8,157,730 B2 | 4/2012 | Leboeuf et al. |
| 8,188,868 B2 | 5/2012 | Case |
| 8,202,148 B2 | 6/2012 | Young |
| 8,290,558 B1 | 10/2012 | Lash et al. |
| 8,294,581 B2 | 10/2012 | Kamen |
| 8,303,311 B2 | 11/2012 | Forest |
| 8,337,013 B2 | 12/2012 | Howell et al. |
| 8,384,617 B2 | 2/2013 | Braun et al. |
| 8,430,507 B2 | 4/2013 | Howell et al. |
| 8,448,846 B2 | 5/2013 | Needhan et al. |
| 8,449,471 B2 | 5/2013 | Tran |
| 8,465,151 B2 | 6/2013 | Howell et al. |
| 8,494,507 B1 | 7/2013 | Tedesco et al. |
| 8,500,271 B2 | 8/2013 | Howell et al. |
| 8,510,166 B2 | 8/2013 | Neven |
| 8,531,355 B2 | 9/2013 | Maltz |
| 8,540,583 B2 | 9/2013 | Leech |
| 8,568,313 B2 | 10/2013 | Sadhu |
| 8,594,971 B2 | 11/2013 | Keal et al. |
| 8,620,600 B2 | 12/2013 | Vock et al. |
| 8,630,633 B1 | 1/2014 | Tedesco et al. |
| 8,634,701 B2 | 1/2014 | Kang et al. |
| 8,647,270 B2 | 2/2014 | Leboeuf et al. |
| 8,690,750 B2 | 4/2014 | Krueger |
| 8,696,113 B2 | 4/2014 | Lewis |
| 8,733,928 B1 | 5/2014 | Lewis |
| 8,750,971 B2 | 6/2014 | Tran |
| 8,764,651 B2 | 7/2014 | Tran |
| 8,849,610 B2 | 9/2014 | Molettiere et al. |
| 8,892,401 B2 | 11/2014 | Yuen et al. |
| 8,905,542 B2 | 12/2014 | Howell et al. |
| 8,911,087 B2 | 12/2014 | Publicover et al. |
| 8,920,332 B2 | 12/2014 | Hong et al. |
| 8,931,896 B2 | 1/2015 | Blum et al. |
| 8,941,560 B2 | 1/2015 | Wong et al. |
| 8,944,590 B2 | 2/2015 | Blum et al. |
| 8,961,415 B2 | 2/2015 | Leboeuf et al. |
| 8,964,298 B2 | 2/2015 | Haddick et al. |
| 8,965,730 B2 | 2/2015 | Yuen |
| 8,979,295 B2 | 3/2015 | Waters |
| 9,001,427 B2 | 4/2015 | Jacobs et al. |
| 9,005,129 B2 | 4/2015 | Venkatraman et al. |
| 9,007,220 B2 | 4/2015 | Johns et al. |
| 9,028,405 B2 | 5/2015 | Tran |
| 9,031,812 B2 | 5/2015 | Roberts et al. |
| 9,033,493 B2 | 5/2015 | Howell et al. |
| 9,035,970 B2 | 5/2015 | Lamb et al. |
| 9,050,033 B2 | 6/2015 | Yoneyama et al. |
| 9,064,342 B2 | 6/2015 | Yuen et al. |
| 9,112,701 B2 | 8/2015 | Sano et al. |
| 9,113,793 B2 | 8/2015 | Terumoto et al. |
| 9,113,794 B2 | 8/2015 | Hong et al. |
| 9,113,795 B2 | 8/2015 | Hong et al. |
| 9,141,194 B1 | 9/2015 | Keyes et al. |
| 9,144,405 B2 | 9/2015 | Kim et al. |
| 9,153,074 B2 | 10/2015 | Zhou et al. |
| 9,215,290 B2 | 12/2015 | Yuen et al. |
| 9,229,227 B2 | 1/2016 | Border et al. |
| 9,235,064 B2 | 1/2016 | Lewis |
| 9,239,473 B2 | 1/2016 | Lewis |
| 9,241,635 B2 | 1/2016 | Yuen et al. |
| 9,244,293 B2 | 1/2016 | Lewis |
| 9,247,212 B2 | 1/2016 | Bose et al. |
| 9,254,100 B2 | 2/2016 | Beck et al. |
| 9,256,711 B2 | 2/2016 | Horseman |
| 9,267,800 B2 | 2/2016 | Doutaz et al. |
| 9,304,331 B2 | 4/2016 | Carrara |
| 9,341,526 B2 | 5/2016 | Bass et al. |
| 9,342,610 B2 | 5/2016 | Liu et al. |
| 9,480,877 B2 | 11/2016 | Chiang et al. |
| 9,520,638 B2 | 12/2016 | Baringer et al. |
| 9,529,197 B2 | 12/2016 | Olsson et al. |
| 9,566,033 B2 | 2/2017 | Bogdanovich et al. |
| 9,579,060 B1 | 2/2017 | Lisy et al. |
| 9,610,476 B1 | 4/2017 | Tran et al. |
| 9,726,904 B1 | 8/2017 | Lin |
| 9,763,592 B2 | 9/2017 | Le et al. |
| 9,782,128 B2 | 10/2017 | Lee et al. |
| 9,896,154 B2 | 2/2018 | Modolo |
| 9,977,259 B2 | 5/2018 | Archambeau et al. |
| 10,092,244 B2 | 10/2018 | Chuang et al. |
| 10,188,323 B2 * | 1/2019 | Sales ................ A61B 5/1114 |
| 10,310,296 B2 | 6/2019 | Howell et al. |
| 10,330,956 B2 | 6/2019 | Howell et al. |
| 10,349,887 B1 | 7/2019 | Tzvieli et al. |
| 10,398,328 B2 | 9/2019 | Kirenko et al. |
| 2001/0031031 A1 | 10/2001 | Ogawa et al. |
| 2002/0151810 A1 | 10/2002 | Wong et al. |
| 2003/0195398 A1 | 10/2003 | Suzuki et al. |
| 2004/0039517 A1 | 2/2004 | Biesinger et al. |
| 2005/0033200 A1 | 2/2005 | Soehren et al. |
| 2005/0036103 A1 | 2/2005 | Bloch |
| 2005/0054942 A1 | 3/2005 | Melker et al. |
| 2006/0115130 A1 | 6/2006 | Kozlay |
| 2007/0052672 A1 | 3/2007 | Ritter et al. |
| 2007/0112287 A1 | 5/2007 | Fancourt et al. |
| 2007/0273611 A1 | 11/2007 | Torch |
| 2008/0137916 A1 | 6/2008 | Lauber et al. |
| 2009/0030350 A1 | 1/2009 | Yang et al. |
| 2009/0195747 A1 | 8/2009 | Insua |
| 2009/0227853 A1 | 9/2009 | Wijesiriwardana |
| 2009/0267805 A1 | 10/2009 | Jin et al. |
| 2010/0042430 A1 | 2/2010 | Bartfeld |
| 2010/0045928 A1 | 2/2010 | Levy |
| 2010/0110368 A1 | 5/2010 | Chaum |
| 2010/0136508 A1 | 6/2010 | Zekhtser |
| 2010/0271587 A1 | 10/2010 | Pavlopoulos |
| 2010/0280336 A1 | 11/2010 | Giftakis et al. |
| 2010/0308999 A1 | 12/2010 | Chornenky |
| 2010/0332571 A1 | 12/2010 | Healey et al. |
| 2011/0169932 A1 | 7/2011 | Mula et al. |
| 2011/0221656 A1 | 9/2011 | Haddick et al. |
| 2011/0224505 A1 | 9/2011 | Sadhu |
| 2012/0021806 A1 | 1/2012 | Maltz |
| 2012/0029367 A1 | 2/2012 | Hobeika |
| 2012/0127423 A1 | 5/2012 | Blum et al. |
| 2012/0133885 A1 | 5/2012 | Howell et al. |
| 2012/0135384 A1 | 5/2012 | Nakao |
| 2012/0142443 A1 | 6/2012 | Savarese et al. |
| 2012/0169990 A1 | 7/2012 | Burnstein |
| 2012/0191016 A1 | 7/2012 | Jastram |
| 2012/0203310 A1 | 8/2012 | Pugh et al. |
| 2012/0206485 A1 | 8/2012 | Osterhout et al. |
| 2012/0310442 A1 | 12/2012 | Doutaz et al. |
| 2013/0009907 A1 | 1/2013 | Rosenberg et al. |
| 2013/0024022 A1 | 1/2013 | Bowers |
| 2013/0024211 A1 | 1/2013 | Monteforte |
| 2013/0041590 A1 | 2/2013 | Burich et al. |
| 2013/0050258 A1 | 2/2013 | Liu et al. |
| 2013/0096397 A1 | 4/2013 | Kiso et al. |
| 2013/0138413 A1 | 5/2013 | Finch et al. |
| 2013/0157232 A1 | 6/2013 | Ehrenkranz |
| 2013/0242262 A1 | 9/2013 | Lewis |
| 2013/0274587 A1 | 10/2013 | Coza et al. |
| 2013/0274904 A1 | 10/2013 | Coza et al. |
| 2013/0307670 A1 | 11/2013 | Ramaci |
| 2013/0329183 A1 | 12/2013 | Blum et al. |
| 2013/0345168 A1 | 12/2013 | Kim et al. |
| 2014/0028456 A1 | 1/2014 | Sadhu |
| 2014/0031703 A1 | 1/2014 | Rayner et al. |
| 2014/0063242 A1 | 3/2014 | Hanina et al. |
| 2014/0073081 A1 | 3/2014 | Wang |

(56) References Cited

U.S. PATENT DOCUMENTS

| | | |
|---|---|---|
| 2014/0078049 A1 | 3/2014 | Parshionikar |
| 2014/0085190 A1 | 3/2014 | Erinjippurath et al. |
| 2014/0135593 A1 | 5/2014 | Jayalth et al. |
| 2014/0142459 A1 | 5/2014 | Jayalth et al. |
| 2014/0159862 A1 | 6/2014 | Yang et al. |
| 2014/0204334 A1 | 7/2014 | Stoll |
| 2014/0207264 A1 | 7/2014 | Quy |
| 2014/0218281 A1 | 8/2014 | Amayeh et al. |
| 2014/0228649 A1 | 8/2014 | Rayner et al. |
| 2014/0229220 A1 | 8/2014 | Yuen et al. |
| 2014/0247145 A1 | 9/2014 | Proud |
| 2014/0266988 A1 | 9/2014 | Fisher et al. |
| 2014/0276096 A1 | 9/2014 | Bonutti |
| 2014/0340221 A1 | 11/2014 | Yuen et al. |
| 2014/0346158 A1 | 11/2014 | Matthews |
| 2014/0375452 A1 | 12/2014 | Yuen et al. |
| 2014/0375470 A1 | 12/2014 | Malveaux |
| 2014/0378872 A1 | 12/2014 | Hong et al. |
| 2015/0057512 A1 | 2/2015 | Kapoor |
| 2015/0065889 A1 | 3/2015 | Gandelman et al. |
| 2015/0085245 A1 | 3/2015 | Howell et al. |
| 2015/0088464 A1 | 3/2015 | Yuen et al. |
| 2015/0148636 A1 | 5/2015 | Benaron |
| 2015/0173631 A1 | 6/2015 | Richards et al. |
| 2015/0179050 A1 | 6/2015 | Katingari et al. |
| 2015/0185506 A1 | 7/2015 | Lewis |
| 2015/0212329 A1 | 7/2015 | Sugihara et al. |
| 2015/0223805 A1 | 8/2015 | Whitman et al. |
| 2015/0244910 A1 | 8/2015 | Marston et al. |
| 2015/0281879 A1 | 10/2015 | Saadi |
| 2015/0287338 A1 | 10/2015 | Wells et al. |
| 2015/0332149 A1 | 11/2015 | Kolb et al. |
| 2015/0342482 A1 | 12/2015 | Carrara |
| 2015/0366518 A1 | 12/2015 | Sampson |
| 2016/0007849 A1 | 1/2016 | Krueger |
| 2016/0034042 A1 | 2/2016 | Joo |
| 2016/0041404 A1 | 2/2016 | Palermo et al. |
| 2016/0041613 A1 | 2/2016 | Klanner et al. |
| 2016/0066848 A1 | 3/2016 | Klosinski, Jr. et al. |
| 2016/0117937 A1 | 4/2016 | Penders et al. |
| 2016/0223577 A1 | 8/2016 | Klosinski, Jr. et al. |
| 2016/0314468 A1 | 10/2016 | Smith et al. |
| 2017/0071528 A1 | 3/2017 | Chen |
| 2017/0255029 A1 | 9/2017 | Klosinski, Jr. et al. |
| 2017/0265798 A1 | 9/2017 | Sales et al. |
| 2017/0323584 A1 | 11/2017 | Daniel et al. |
| 2018/0014737 A1 | 1/2018 | Paulussen et al. |
| 2018/0064399 A1 | 3/2018 | Buettgen et al. |
| 2018/0081201 A1 | 3/2018 | Lore et al. |
| 2019/0216340 A1 | 7/2019 | Holz |

FOREIGN PATENT DOCUMENTS

| | | |
|---|---|---|
| WO | 2005015163 | 2/2005 |
| WO | 2005094667 | 10/2005 |
| WO | 2007088374 | 8/2007 |
| WO | 2008073806 | 6/2008 |
| WO | 2010006370 | 1/2010 |
| WO | 2010062479 | 6/2010 |
| WO | 2010062481 | 6/2010 |
| WO | 2011086466 | 7/2011 |
| WO | 2012041485 | 4/2012 |
| WO | 2013188343 | 12/2013 |
| WO | 2014021602 | 2/2014 |
| WO | 2014108481 | 7/2014 |
| WO | 2014144918 | 9/2014 |
| WO | 2014144940 | 9/2014 |
| WO | 2014170280 | 10/2014 |
| WO | 2014188244 | 11/2014 |
| WO | 2015015025 | 2/2015 |
| WO | 2015081299 | 6/2015 |
| WO | 2015095924 | 7/2015 |
| WO | 2015127143 | 8/2015 |
| WO | 2015127441 | 8/2015 |
| WO | 2016017997 | 2/2016 |
| WO | 2016029803 | 3/2016 |

OTHER PUBLICATIONS

Final Office Action, dated Dec. 15, 2016, from corresponding U.S. Appl. No. 14/506,249.
Final Office Action, dated Dec. 31, 2018, from corresponding U.S. Appl. No. 14/550,406.
Final Office Action, dated Jan. 14, 2019, from corresponding U.S. Appl. No. 14/578,039.
Final Office Action, dated Jan. 14, 2019, from corresponding U.S. Appl. No. 15/060,333.
Final Office Action, dated Jul. 10, 2017, from corresponding U.S. Appl. No. 14/846,401.
Final Office Action, dated Jun. 14, 2018, from corresponding U.S. Appl. No. 15/074,679.
Final Office Action, dated Jun. 30, 2017, from corresponding U.S. Appl. No. 14/610,589.
Final Office Action, dated Mar. 2, 2018, from corresponding U.S. Appl. No. 15/060,333.
Final Office Action, dated Mar. 29, 2017, from corresponding U.S. Appl. No. 14/562,454.
Final Office Action, dated Mar. 30 2018, from corresponding U.S. Appl. No. 14/846,401.
Final Office Action, dated May 23, 2017, from corresponding U.S. Appl. No. 14/578,039.
Final Office Action, dated Nov. 16, 2017, from corresponding U.S. Appl. No. 14/610,628.
Final Office Action, dated Sep. 25, 2018, from corresponding U.S. Appl. No. 14/610,439.
Final Office Action, dated Sep. 26, 2016, from corresponding U.S. Appl. No. 14/610,628.
International Preliminary Report on Patentability, dated Mar. 16, 2017, from corresponding International Application No. PCT/US2015/048612.
International Preliminary Report on Patentability, dated Mar. 16, 2017, from corresponding International Application No. PCT/US2015/048656.
International Preliminary Report on Patentability, dated Mar. 16, 2017, from corresponding International Application No. PCT/US2015/048662.
International Search Report, dated Dec. 18, 2015, from corresponding International Application No. PCT/US2015/048662.
International Search Report, dated Jan. 21, 2016, from corresponding International Application No. PCT/US2015/048612.
International Search Report, dated Jan. 21, 2016, from corresponding International Application No. PCT/US2015/048656.
International Search Report, dated Jun. 2, 2016, from corresponding International Application No. PCT/US2016/015705.
Invitation to Pay Additional Search Fees, dated Apr. 1, 2016, from corresponding International Application Serial No. PCT/US2016/015705.
Invitation to Pay Additional Search Fees, dated Nov. 4, 2015, from corresponding International Application Serial No. PCT/US2015/048612.
Invitation to Pay Additional Search Fees, dated Nov. 4, 2015, from corresponding International Application Serial No. PCT/US2015/048656.
Jeannet, Pierre-Yves, et al., "Continuous monitoring and quantification of multiple parameters of daily physical activity in ambulatory Duchenne muscular , dystrophy patients", Official Journal of the European Paediatric Neurology Society, 2011.
Maria S. Redin, "Marathon Man", Article Jun. 15, 1998, MIT Media Laboratory.
Michael Franco, Tzoa wearable turns you into a walking air-quality sensor, Dec. 9, 2014, CNET, https://www.cnet.com/news/tzoa-wearable-turns-you-into-a-walking-air-quality-sensor/.
Notice of Allowance, dated Dec. 13, 2017, from corresponding U.S. Appl. No. 14/610,501.

(56) References Cited

OTHER PUBLICATIONS

Notice of Allowance, dated Feb. 28, 2017, from corresponding U.S. Appl. No. 14/588,122.
Notice of Allowance, dated Jan. 17, 2019, from corresponding U.S. Appl. No. 14/610,439.
Notice of Allowance, dated Jun. 21, 2017, from corresponding U.S. Appl. No. 14/562,454.
Notice of Allowance, dated Oct. 11, 2018, from corresponding U.S. Appl. No. 15/074,679.
Notice of Allowance, dated Oct. 20, 2017, from corresponding U.S. Appl. No. 15/489,147.
Notice of Allowance, dated Sep. 13, 2018, from corresponding U.S. Appl. No. 15/594,898.
Office Action, dated Aug. 19, 2016, from corresponding U.S. Appl. No. 14/578,039.
Office Action, dated Aug. 7, 2018, from corresponding U.S. Appl. No. 14/550,406.
Office Action, dated Dec. 29, 2016, from corresponding U.S. Appl. No. 14/610,589.
Office Action, dated Feb. 10, 2017, from corresponding U.S. Appl. No. 14/846,401.
Office Action, dated Jan. 11, 2018, from corresponding U.S. Appl. No. 15/074,679.
Office Action, dated Jul. 1, 2016, from corresponding U.S. Appl. No. 14/562,454.
Office Action, dated Jul. 22, 2016, from corresponding U.S. Appl. No. 14/506,249.
Office Action, dated Jun. 27, 2017, from corresponding U.S. Appl. No. 15/060,333.
Office Action, dated Jun. 29, 2017, from corresponding U.S. Appl. No. 15/489,147.
Office Action, dated Jun. 8, 2018, from corresponding U.S. Appl. No. 14/610,501.
Office Action, dated Mar. 3, 2017, from corresponding U.S. Appl. No. 14/610,628.
Office Action, dated Mar. 8, 2016, from corresponding U.S. Appl. No. 14/610,628.
Office Action, dated Mar. 9, 2018, from corresponding U.S. Appl. No. 14/610,439.
Office Action, dated May 23, 2018, from corresponding U.S. Appl. No. 14/578,039.
Office Action, dated Nov. 30, 2017, from corresponding U.S. Appl. No. 14/550,406.
Office Action, dated Oct. 4, 2018, from corresponding U.S. Appl. No. 15/791,196.
Office Action, dated Sep. 11, 2018, from corresponding U.S. Appl. No. 15/060,333.
Office Action, dated Sep. 2, 2016, from corresponding U.S. Appl. No. 14/588,122.
Office Action, dated Sep. 26, 2017, from corresponding U.S. Appl. No. 14/846,401.
Office Action, dated Sep. 29, 2017, from corresponding U.S. Appl. No. 14/506,249.
Phend, Crystal, "Calorie Intake Rises as Sleep Time Drops," Medpage Today, Medpage Today, LLC, Mar. 15, 2012, Web Dec. 19, 2016, http://www.medpagetoday.com/cardiology/prevention/31663.
Restriction Requirement, dated Nov. 10, 2016, from corresponding U.S. Appl. No. 14/846,401.
Restriction Requirement, dated Oct. 4, 2017, from corresponding U.S. Appl. No. 14/610,439.
Restriction Requirement, dated Sep. 13, 2017, from corresponding U.S. Appl. No. 14/550,406.
Richard M. Satava, et al., "The Physiologic Cipher at Altitude: Telemedicine and Real-Time Monitoring of Climbers on Mount Everest", Telemedicine Journal and e-Health, vol. 6, No. 3, 2000, Mary Ann Liebert, Inc.
Shankland, Stephen, "Google's electronic eyewear get 'OK Glass' voice commands", Feb. 20, 2013, Cnet.com, https://www.cnet.com/news/googles-electronic-eyewear-gets-ok-glass-voice-commands/.
Ted Burnham, Wearable Air Quality Sensor: Tzoa, Jan. 5, 2015, Postscapes, http://www.postscapes.com/wearable-air-quality-sensor-tzoa/.
Tolentino, Mellisa, Udderly Clever Wearable Tech Solutions, http://siliconangle.com/blog/2014/03/25/udderly-clever-wearable-tech-solutions/, Mar. 25, 2014.
Torres, Juan Carlos, ODG R-7 Smart Glasses Carries Its Own Android Inside, http://androidcommunity.com/odg-r-7-smart-glasses-carries-its-own-android-inside-20140919/, Sep. 19, 2014.
Written Opinion of the International Searching Authority, dated Dec. 18, 2015, from corresponding International Application No. PCT/US2015/048662.
Written Opinion of the International Searching Authority, dated Jan. 21, 2016, from corresponding International Application No. PCT/US2015/048612.
Written Opinion of the International Searching Authority, dated Jan. 21, 2016, from corresponding International Application No. PCT/US2015/048656.
Written Opinion of the International Searching Authority, dated Jun. 2, 2016, from corresponding International Application No. PCT/US2016/015705.
Notice of Allowance, dated Jun. 5, 2019, from corresponding U.S. Appl. No. 14/550,406.
Office Action, dated Jun. 11, 2019, from corresponding U.S. Appl. No. 14/610,501.
Office Action, dated Jun. 27, 2019, from corresponding U.S. Appl. No. 15/060,333.
Office Action, dated Feb. 11, 2019, from corresponding U.S. Appl. No. 14/846,401.
Office Action, dated Apr. 4, 2019, from corresponding U.S. Appl. No. 16/284,615.
Final Office Action, dated Apr. 29, 2019, from corresponding U.S. Appl. No. 15/791,196.
Final Office Action, dated Jul. 18, 2019, from corresponding U.S. Appl. No. 14/846,401.
Notice of Allowance, dated Jul. 31, 2019, from corresponding U.S. Appl. No. 16/284,615.
Office Action, dated Aug. 6, 2019, from corresponding U.S. Appl. No. 16/429,480.
Office Action, dated Aug. 7, 2019, from corresponding U.S. Appl. No. 15/611,574.
Office Action, dated Oct. 4, 2019, from corresponding U.S. Appl. No. 15/791,196.
Office Action, dated Nov. 15, 2019, from corresponding U.S. Appl. No. 16/527,544.

* cited by examiner

SYSTEMS, APPARATUS, AND METHODS FOR USING A WEARABLE DEVICE TO CONFIRM THE IDENTITY OF AN INDIVIDUAL

CROSS-REFERENCE TO RELATED APPLICATIONS

This application is a continuation of U.S. patent application Ser. No. 15/594,898, filed May 15, 2017, now U.S. Pat. No. 10,188,323 entitled "Systems, Apparatus, and Methods for Using Eyewear, or Other Wearable Item, to Confirm the Identity of an Individual," which is a divisional of U.S. patent application Ser. No. 14/588,122, filed Dec. 31, 2014, now U.S. Pat. No. 9,649,052, issued May 16, 2017, entitled "Systems, Apparatus, and Methods for Using Eyewear, or Other Wearable Item, to Confirm the Identity of an individual," which claims the benefit of U.S. Provisional Patent Application Ser. No. 62/046,406, filed Sep. 5, 2014, entitled "Wearable Health Computer Apparatus, Systems, and Related Methods," the disclosures of which are hereby incorporated by reference herein in their entirety.

BACKGROUND

Currently, users must often provide a password and/or produce other identifying information to gain access to a particular computer system, particular computer program, or to a particular building or secure area within a building. This can be inconvenient and time consuming. Accordingly, there is a need for improved systems, apparatus, and methods for facilitating access, by an individual, to computer systems, computer programs, and secure areas.

SUMMARY OF THE VARIOUS EMBODIMENTS

It should be appreciated that this Summary is provided to introduce a selection of concepts in a simplified form that are further described below in the Detailed Description. This Summary is not intended to be used to limit the scope of the claimed subject matter.

According to a first aspect of the disclosure, a computer-implemented method is provided for providing a particular individual with access to a computer system or computer program. The method includes receiving a wireless signal from a wearable device. The wireless signal includes a unique identifier associated with the particular person. In response to receiving the wireless signal, the unique identifier is compared with a stored identifier for the particular individual. In response to determining that the unique identifier at least partially matches the stored identifier, the particular individual is provided with access to the computer system or computer program.

According to another aspect, a system for confirming an identity of an individual is provided. The system includes a wearable device having one or more processors, one or more sensors in communication with the processors, and at least one electronic communications device in communication with the processors. The electronic communications device is adapted to broadcast a wireless signal that has a unique identifier associated with a particular individual wearing the wearable device. The wireless signal is configured to be received by a remote computer system that uses the unique identifier to compare to a stored identifier for the particular individual so that the remote computer system can allow the particular individual access to one of the remote computer system, a secure area associated with the remote computer system, or a payment system associated with the remote computer system.

According to yet another aspect, a system for confirming an identity of an individual is provided. The system includes a wearable device having one or more processors operative to receive a unique identifier associate with the individual from one or more sensors. The system also includes one or more electronic communications devices in communication with the processors and configured to broadcast a wireless signal that has a unique identifier associated with the individual wearing the wearable device. The wireless signal is configured to be received by a remote computer system that uses the unique identifier to compare to a stored identifier for the individual so that the remote computer system can allow the individual access to one of the remote computer system, a secure area associated with the remote computer system, or a payment system associated with the remote computer system.

The features, functions, and advantages that have been discussed can be achieved independently in various embodiments of the present disclosure or may be combined in yet other embodiments, further details of which can be seen with reference to the following description and drawings.

BRIEF DESCRIPTION OF THE DRAWINGS

Various embodiments of systems and methods for confirming the identity of an individual are described below. In the course of this description, reference will be made to the accompanying drawings, which are not necessarily drawn to scale and wherein.

DETAILED DESCRIPTION OF SOME EMBODIMENTS

Figure 1:
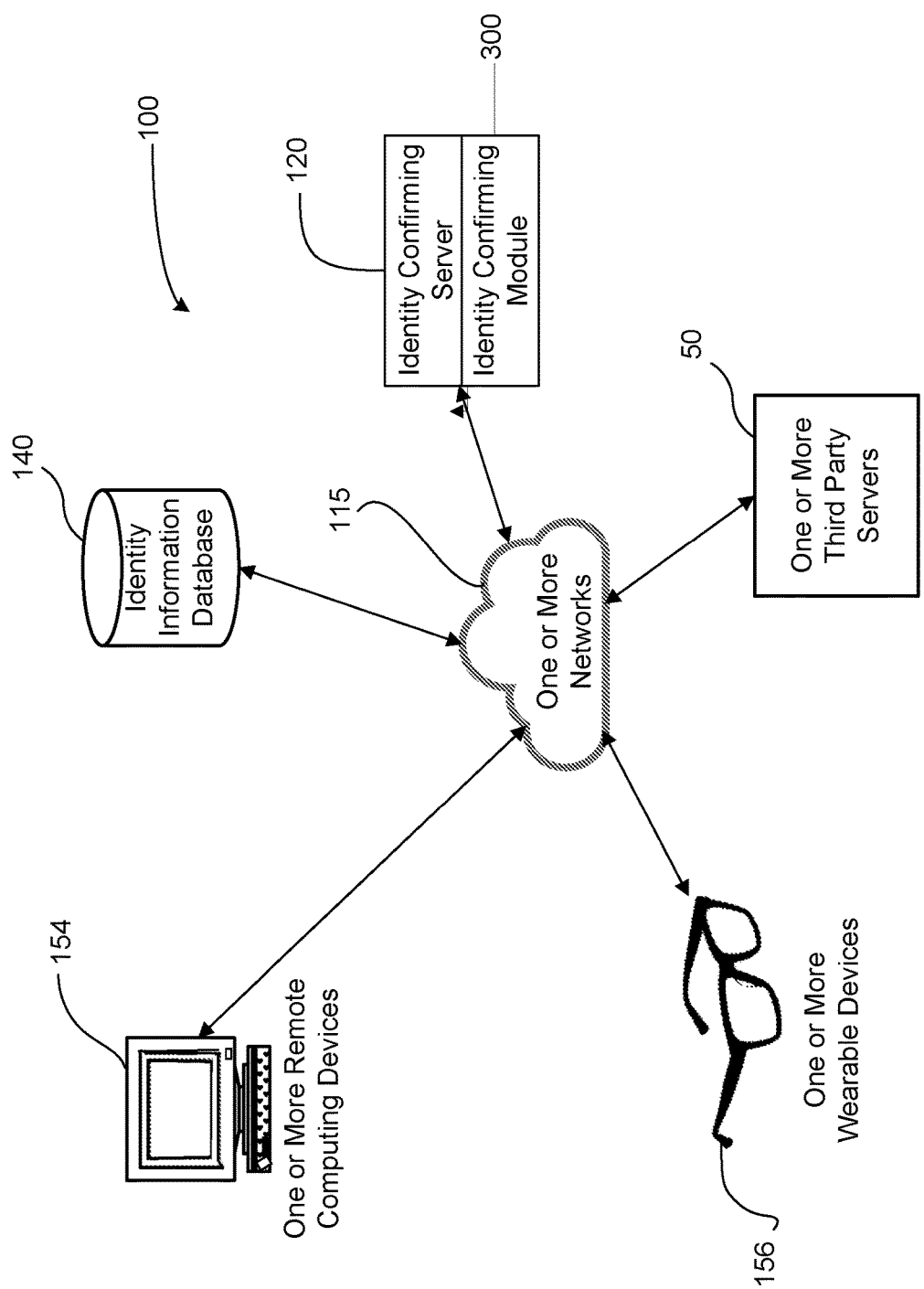
FIG. 1 is a block diagram of an Identity Confirmation System in accordance with an embodiment of the present system.

Various embodiments will now be described more fully hereinafter with reference to the accompanying drawings. It should be understood that the invention may be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Overview

Eyewear, according to various embodiments, includes one or more electronic devices (or other devices) that are used to confirm the identity of the wearer and to facilitate identifying the wearer of the eyewear to one or more individuals or computing devices. For example, the eyewear may include one or more biometric sensors that are adapted for selectively confirming that the individual wearing the eyewear is, in fact, the owner of the eyewear (or other specific individual associated with the eyewear). In various embodiments, the eyewear may be configured to, at least partially in response to confirming the individual's identity, communicate the individual's identity to a remote computing device. The eyewear may do this, for example, by broadcasting a unique identification code associated with the user via Near Field Communications, Bluetooth, or any other suitable wireless communications technology. This may be useful, for example, in allowing a user to access a computing system or secure area without presenting any other form of physical identification, and/or without entering a password or passcode.

A wearable identity confirmation system, in various embodiments, may, for example, be embodied in any suitable wearable device configured to confirm the identity of a wearer. The system may, for example, be embodied as a pair of eyewear (e.g., eyeglasses or goggles), contact lenses, a wristwatch, a suitable piece of clothing (e.g., such as a suitable shirt, pair of pants, undergarment, compression sleeve, etc.), footwear, a hat, a helmet, an orthopedic cast, or any other suitable wearable item. In a particular example, an identity confirmation system is embodied as a pair of computerized eyewear.

In various embodiments, the system comprises one or more sensors configured to determine the wearer's identity. The one or more sensors may be coupled to the wearable device in any suitable way. For instance, the one or more sensors may be embedded into the wearable device, and/or operatively coupled to the wearable device. The one or more sensors may include, for example, one or more wireless communications devices (e.g., one or more near field communications devices (e.g., an NFC Chip), one or more Bluetooth devices (e.g., a Bluetooth chip)), one or more GPS units, one or more RFID tags, one or more fingerprint readers, one or more iris readers, one or more retinal scanners, one or more voice recognition systems, one or more heart rate monitors, one or more electrocardiogram (EKG) sensors, one or more electroencephalograms (EEGs), one or more pedometers, one or more thermometers, one or more transdermal transmitter sensors, one or more front-facing cameras, one or more eye-facing cameras, one or more microphones, one or more accelerometers, one or more blood pressure sensors, one or more pulse oximeters, one or more respiratory rate sensors, one or more blood alcohol concentration (BAC) sensors, one or more near-field communication sensors, one or more motion sensors, one or more gyroscopes, one or more geomagnetic sensors, one or more global position system (GPS) sensors, one or more impact sensors, one or more tear sensors, one or more DNA and/or genome sampling devices (e.g., a "lab on a chip" system that may sample and/or analyze DNA and/or genome information for an individual), and/or any other suitable sensors (e.g., any other suitable biometric sensors). In particular embodiments, the system is configured to gather and store data, for example, using the one or more sensors, about the wearer (e.g., such as the wearer's facial contours, iris patterns, overall facial image, body temperature, user DNA and/or genome sequence information, balance, heart rate, level of activity, position, body motion, facial muscle movements, etc.).

Exemplary Technical Platforms

As will be appreciated by one skilled in the relevant field, the present systems and methods may be, for example, embodied as a computer system, a method, or a computer program product. Accordingly, various embodiments may be entirely hardware or a combination of hardware and software. Furthermore, particular embodiments may take the form of a computer program product stored on a computer-readable storage medium having computer-readable instructions (e.g., software) embodied in the storage medium. Various embodiments may also take the form of web-implemented computer software. Any suitable computer-readable storage medium may be utilized including, for example, hard disks, compact disks, DVDs, optical storage devices, and/or magnetic storage devices.

Various embodiments are described below with reference to block diagram and flowchart illustrations of methods, apparatuses, (e.g., systems), and computer program products. It should be understood that each block of the block diagrams and flowchart illustrations, and combinations of blocks in the block diagrams and flowchart illustrations, respectively, can be implemented by a computer executing computer program instructions. These computer program instructions may be loaded onto a general purpose computer, a special purpose computer, or other programmable data processing apparatus that can direct a computer or other programmable data processing apparatus to function in a particular manner such that the instructions stored in the computer-readable memory produce an article of manufacture that is configured for implementing the functions specified in the flowchart block or blocks.

The computer instructions may execute entirely on the user's computer, partly on the user's computer, as a stand-alone software package, partly on a user's computer and partly on a remote computer, or entirely on the remote computer or server. In the latter scenario, the remote computer may be connected to the user's computer through any type of network, including but not limited to: a local area network (LAN); a wide area network (WAN); a cellular network; or the connection may be made to an external computer (for example, through the Internet using an Internet Service Provider).

These computer program instructions may also be stored in a computer-readable memory that can direct a computer or other programmable data processing apparatus to function in a particular manner such that the instructions stored in the computer-readable memory produce an article of manufacture that is configured for implementing the function specified in the flowchart block or blocks. The computer program instructions may also be loaded onto a computer or other programmable data processing apparatus to cause a series of operational steps to be performed on the computer or other programmable apparatus to produce a computer-implemented process (e.g., method) such that the instructions that execute on the computer or other programmable apparatus provide steps for implementing the functions specified in the flowchart block or blocks.

Exemplary System Architecture

FIG. 1 is a block diagram of an Identity Confirmation System 100 according to particular embodiments. As may be understood from this figure, the Identity Confirmation System 100 includes one or more Networks 115, one or more Third Party Servers 50, an Identity Confirmation Server 120 that may, for example, be adapted to execute an Identity Confirmation Module 300, a Database 140, one or more Remote Computing Devices 154 (e.g., such as a smart phone, a tablet computer, a wearable computing device, a laptop computer, a desktop computer, etc.), and one or more Wearable Devices 156, which may, for example, be embodied as one or more of eyewear, headwear, clothing, a watch, a hat, a helmet, a cast, an adhesive bandage, a piece of jewelry (e.g., a ring, earring, necklace, bracelet, etc.), or any other suitable wearable device. In particular embodiments, the one or more computer networks 115 facilitate communication between the one or more Third Party Servers 50, the Identity Confirmation Server 120, Database 140, one or more Remote Computing Devices 154, and the one or more Wearable Devices 156.

The one or more networks 115 may include any of a variety of types of wired or wireless computer networks such as the Internet, a private intranet, a mesh network, a public switch telephone network (PSTN), or any other type of network (e.g., a network that uses Bluetooth or near field communications to facilitate communication between computing devices). The communication link between the one or more Remote Computing Devices 154 and the Identity Confirmation Server 120 may be, for example, implemented via a Local Area Network (LAN) or via the Internet.

Figure 2:
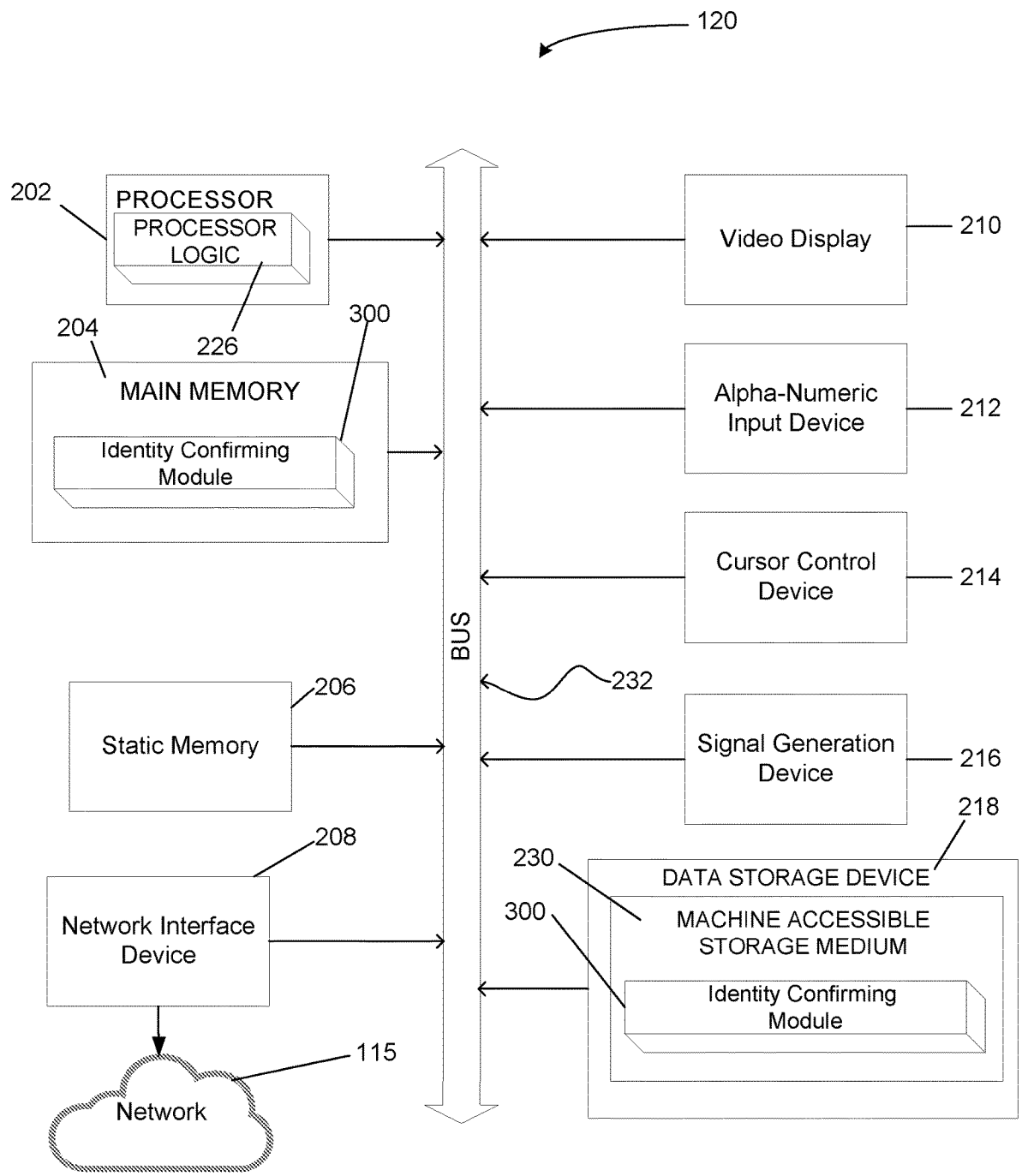
FIG. 2 is a block diagram of the Identity Confirmation Server of FIG. 1.

FIG. 2 illustrates a diagrammatic representation of the architecture for the Identity Confirmation Server 120 that may be used within the Identity Confirmation System 100. It should be understood that the computer architecture shown in FIG. 2 may also represent the computer architecture for any one of the one or more Remote Computing Devices 154, one or more Third Party Servers 50, and one or more Wearable Devices 156 shown in FIG. 1. In particular embodiments, the Identity Confirmation Server 120 may be suitable for use as a computer within the context of the Identity Confirmation System 100 that is configured for confirming the identity of a wearer by detecting characteristics of the wearer or the one or more Wearable Devices 156 using signals received from sensors coupled to the one or more Wearable Devices 156.

In particular embodiments, the Identity Confirmation Server 120 may be connected (e.g., networked) to other computing devices in a LAN, an intranet, an extranet, and/or the Internet as shown in FIG. 1. As noted above, the Identity Confirmation Server 120 may operate in the capacity of a server or a client computing device in a client-server network environment, or as a peer computing device in a peer-to-peer (or distributed) network environment. The Identity Confirmation Server 120 may be a desktop personal computing device (PC), a tablet PC, a set-top box (STB), a Personal Digital Assistant (PDA), a cellular telephone, a web appliance, a network router, a switch or bridge, or any other computing device capable of executing a set of instructions (sequential or otherwise) that specify actions to be taken by that computing device. Further, while only a single computing device is illustrated, the term "computing device" shall also be interpreted to include any collection of computing devices that individually or jointly execute a set (or multiple sets) of instructions to perform any one or more of the methodologies discussed herein.

An exemplary Identity Confirmation Server 120 includes a processing device 202, a main memory 204 (e.g., read-only memory (ROM), flash memory, dynamic random access memory (DRAM) such as synchronous DRAM (SDRAM) or Rambus DRAM (RDRAM), etc.), a static memory 206 (e.g., flash memory, static random access memory (SRAM), etc.), and a data storage device 218, which communicate with each other via a bus 232.

The processing device 202 represents one or more general-purpose or specific processing devices such as a microprocessor, a central processing unit (CPU), or the like. More particularly, the processing device 202 may be a complex instruction set computing (CISC) microprocessor, reduced instruction set computing (RISC) microprocessor, very long instruction word (VLIW) microprocessor, or processor implementing other instruction sets, or processors implementing a combination of instruction sets. The processing device 202 may also be one or more special-purpose processing devices such as an application specific integrated circuit (ASIC), a field programmable gate array (FPGA), a digital signal processor (DSP), network processor, or the like. The processing device 202 may be configured to execute processing logic 226 for performing various operations and steps discussed herein.

The Identity Confirmation Server 120 may further include a network interface device 208. The Identity Confirmation Server 120 may also include a video display unit 210 (e.g., a liquid crystal display (LCD) or a cathode ray tube (CRT)), an alpha-numeric input device 212 (e.g., a keyboard), a cursor control device 214 (e.g., a mouse), and a signal generation device 216 (e.g., a speaker).

The data storage device 218 may include a non-transitory computing device-accessible storage medium 230 (also known as a non-transitory computing device-readable storage medium, a non-transitory computing device-readable medium, or a non-transitory computer-readable medium) on which is stored one or more sets of instructions (e.g., the Identity Confirmation Module 300) embodying any one or more of the methodologies or functions described herein. The one or more sets of instructions may also reside, completely or at least partially, within the main memory 204 and/or within the processing device 202 during execution thereof by the Identity Confirmation Server 120—the main memory 204 and the processing device 202 also constituting computing device-accessible storage media. The one or more sets of instructions may further be transmitted or received over a network 115 via a network interface device 208.

While the computing device-accessible storage medium 230 is shown in an exemplary embodiment to be a single medium, the term "computing device-accessible storage medium" (or "computer readable medium") should be understood to include a single medium or multiple media (e.g., a centralized or distributed database, and/or associated caches and servers) that store the one or more sets of instructions. The term "computing device-accessible storage medium" should also be understood to include any medium that is capable of storing, encoding, or carrying a set of instructions for execution by the computing device and that causes the computing device to include any one or more of the methodologies of the present invention. The term "computing device-accessible storage medium" should accordingly be understood to include, but not be limited to, solid-state memories, optical and magnetic media, etc.

Exemplary System Platform

As noted above, a system, according to various embodiments, is adapted to confirm the identity of a wearer of a wearable device. Various aspects of the system's functionality may be executed by certain system modules, including Identity Confirmation Module 300. The Identity Confirmation Module 300 is discussed in greater detail below.

Identity Confirmation Module

Figure 3:
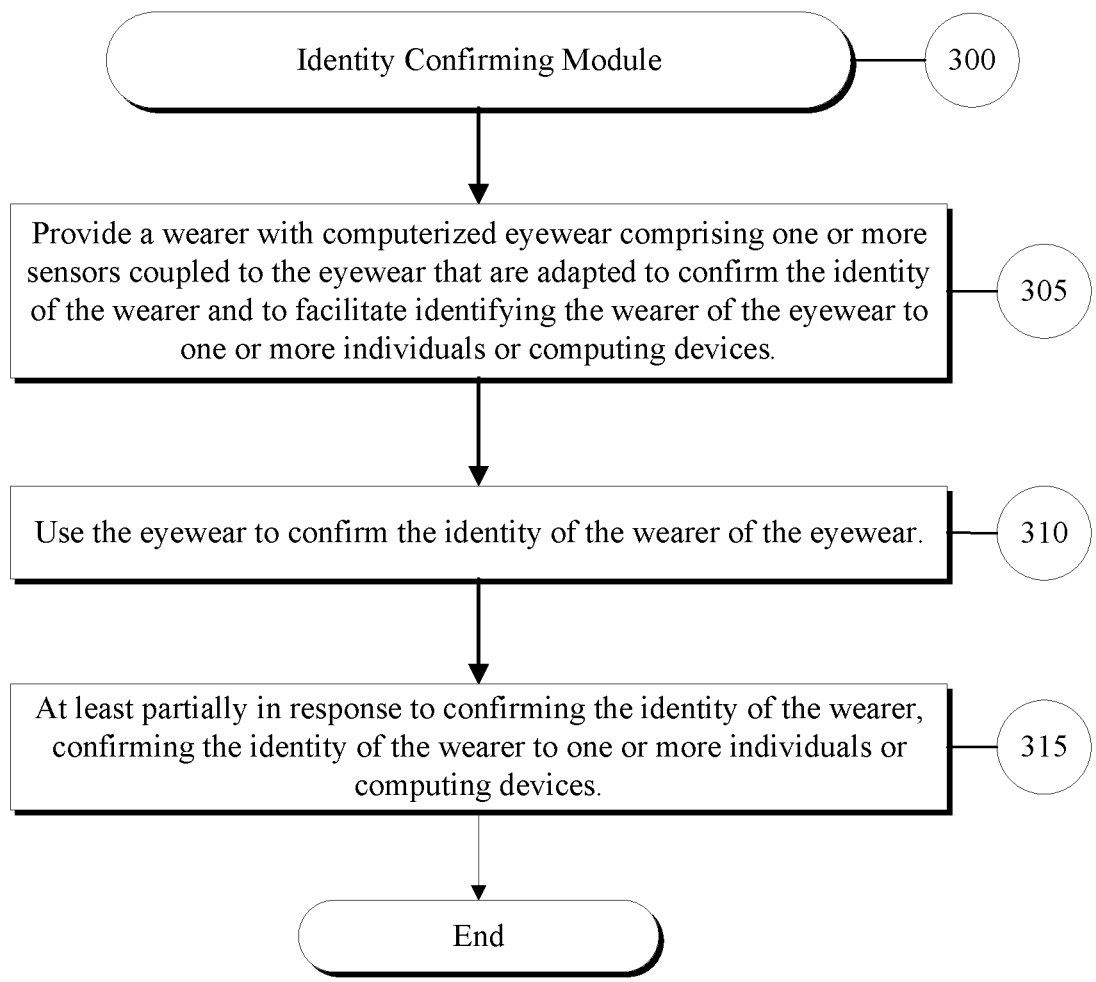
FIG. 3 depicts a flowchart that generally illustrates various steps executed by an Identity Confirmation Module according to a particular embodiment.

FIG. 3 is a flow chart of operations performed by an exemplary Identity Confirmation Module 300, which may, for example, run on the Identity Confirmation Server 120, or any suitable computing device (such as the one or more Wearable Devices 156 or a suitable mobile computing device). In particular embodiments, the Identity Confirmation Module 300 may confirm a wearer's identity and may communicate the wearer's identity to a remote computing device.

The system begins, in various embodiments, at Step 305 by providing a wearer with computerized eyewear comprising one or more sensors coupled to the eyewear that are adapted to confirm the identity of the wearer and to facilitate identifying the wearer of the eyewear to one or more individuals and/or computing devices. In various embodiments, the system may do this by, for example: (1) facilitating delivery of the eyewear to an address associated with a particular individual; (2) facilitating distribution of the eyewear from a healthcare worker to the individual; and (3) placing an order of the eyewear from a third party for delivery to the individual. In other embodiments, this step may be executed manually (e.g., by a human being) rather than a computer.

The system continues, at Step 310 by using the eyewear to confirm the identity of the wearer of the eyewear. In various embodiments, the eyewear may confirm the identity of the wearer in any suitable way. In particular embodiments, the eyewear may confirm the identity of the wearer using one or more facial characteristics of the wearer. In other embodiments, the eyewear may confirm the identity of the wearer using biometric data received from the one or more sensors (e.g., a fingerprint sensor, an iris scanner, a tear or blood sampling device, a DNA and/or genome testing device etc. . . . ). In further embodiments, the eyewear may confirm the identity of the wearer by requesting a password (e.g., an alphanumeric password) from the wearer, receiving a password from the wearer via any suitable input device (e.g., a keyboard, camera, or microphone), and verifying that the password matches a password associated with the wearer. In some embodiments, the eyewear may confirm the identity of the wearer using voice recognition techniques, or any other suitable identity confirmation technique.

In some embodiments, the eyewear may confirm the identity of the wearer substantially automatically after the wearer puts the eyewear on. Also, in particular embodiments, the eyewear may confirm the identity of the wearer on a substantially periodic basis (e.g., once per second, once per minute, once per hour, once per day, etc.). For example, the eyewear may confirm the identity of the wearer every thirty seconds throughout the day. In other embodiments, the eyewear may confirm the identity of the wearer at least partially in response to receiving an indication from the wearer that the eyewear should confirm the identity of the wearer. For instance, the wearer may speak a voice command to the wearable device requesting that the device scan the wearer's iris. In various embodiments, the eyewear may receive an indication from the wearer of when to have the eyewear confirm the identity of the wearer. For example, the eyewear may receive an indication from the wearer to have the eyewear conduct a retinal scan of the user (e.g., receive at least one retinal scan) at 8:00 a.m. and at 2:00 p.m. on a particular day. In other embodiments, the eyewear may confirm the identity of the wearer according to an established schedule. In some embodiments, the established schedule may be determined randomly. For example, the established schedule may be different each day that the eyewear confirms the identity of the wearer.

In particular embodiments, the eyewear may receive a request from the wearer to have particular biometric data received from a particular sensor at the same time that the eyewear receives a second particular biometric data from a second particular sensor. For example, when the eyewear receives biometric data for the wearer's fingerprint, the eyewear may, at least partially in response to receiving the fingerprint data, also obtain iris data of the wearer's eye from an iris reader associated with the eyewear. As a further example, the eyewear may be configured to simultaneously receive biometric data from both an eye-facing camera and a fingerprint reader associated with the eyewear.

In various embodiments, the eyewear may receive singular biometric data from a single sensor associated with the eyewear. For example, the eyewear may receive a single iris scan from the iris reader. In other embodiments, the eyewear may receive singular biometric data from a plurality of the sensors associated with the eyewear. For instance, the eyewear may receive an iris scan from the iris reader, a fingerprint from the fingerprint reader, and a body temperature from the thermometer. In yet other embodiments, the system may receive multiple sets of biometric data from one or more of the sensors. For example, the eyewear may receive multiple fingerprints from the fingerprint reader and/or multiple temperature readings from the thermometer. In various embodiments, the eyewear, or other computer, may facilitate storing the received biometric data in the Identity Information Database 140. In some embodiments, the eyewear, or other computing device, may associate the received biometric data with an account associated with the wearer. In other embodiments, the eyewear, or other computing device, may associated the received biometric data with an account associated with the eyewear.

In particular embodiments, the eyewear may confirm the identity of the wearer by comparing the received biometric data to the stored biometric data. In some embodiments, the eyewear may confirm the identity of the wearer based on the comparison between the received biometric data and the stored biometric data only when there is a complete match between the received biometric data and the stored biometric data. In other embodiments, the eyewear may confirm the identity of the wearer based on the comparison between the received biometric data and the stored biometric data when there is at least a partial match between the received biometric data and the stored biometric data (e.g., at least a predetermined percentage of the received biometric data matches the stored biometric data). For instance, the eyewear may confirm the identity of the wearer in response to at least about 90 percent of the received biometric data matching the stored biometric data. In particular embodiments, the eyewear may use any suitable algorithm to confirm the identity of the wearer.

In various embodiments, the eyewear may confirm the identity of the wearer using a single set of biometric data. For instance, the eyewear may confirm the identity of the wearer using only the wearer's fingerprint. In other embodiments, the eyewear may require a plurality of sets of biometric data to confirm the identity of the wearer. For example, the eyewear may only confirm the identity of the wearer after receiving a fingerprint, an iris reading, and a retinal scan (or other eye scan) for the wearer.

At Step 315, at least partially in response to confirming the identity of the wearer, the eyewear confirms the identity of the wearer to one or more individuals and/or computing devices. In various embodiments, the eyewear may confirm the identity of the wearer to one or more individuals or computing devices by broadcasting a unique identifier associated with the wearer. In some embodiments, the eyewear may broadcast the unique identifier associated with the wearer to one or more individuals or computing devices substantially automatically at least partially in response to the eyewear confirming the identity of the wearer. In other embodiments, the eyewear may broadcast the unique identifier associated with the wearer to one or more individuals or computing devices on a substantially periodic basis (e.g., by the second, by the minute, hourly, daily, etc.). For example, the eyewear may broadcast the identity of the wearer to one or more individuals or computing devices every thirty seconds throughout the day. In yet other embodiments, the eyewear may broadcast the identity of the wearer to one or more individuals or computing devices substantially continuously (e.g., once every second substantially without pause). In some embodiments, the eyewear may broadcast the identity of the wearer to one or more individuals or computing devices according to a predetermined schedule.

In various embodiments, the eyewear may broadcast (e.g., wirelessly broadcast) the identity of the wearer to one or more individuals and/or computing devices at least partially in response to receiving an indication from the wearer that the eyewear should broadcast the identity of the wearer to one or more individuals or computing devices. For instance, the wearer may speak a voice command to the wearable device requesting that the device broadcast the wearer's identity to a remote computing device. In yet other embodiments, the eyewear may broadcast the identity of the wearer to one or more individuals or computing devices at least partially in response to receiving an indication from the one or more individuals or computing devices that the eyewear should broadcast the identity of the wearer. For instance, a particular remote computing device may send a request to the wearable device to broadcast the wearer's identity. In various embodiments, the eyewear may receive an indication from the wearer of when to have the eyewear broadcast the identity of the wearer to the one or more individuals or computing devices. For example, the eyewear may receive an indication from the wearer to have the eyewear broadcast the wearer's identity to a remote computing device at 8:00 a.m. and at 2:00 p.m. every weekday (e.g., Monday, Tuesday, Wednesday, Thursday, Friday).

In particular embodiments, the one or more individuals receiving the wearer's broadcast identity information may be the owner of the eyewear, the wearer's employer, the parent and/or guardian of the wearer, etc. In other embodiments, the one or more computing devices receiving the wearer's broadcast identity information may be any suitable computing device (e.g., such as a smart phone, a tablet computer, a wearable computing device, a laptop computer, a desktop computer, etc.). In some embodiments, the eyewear may broadcast the identity of the wearer to the one or more individuals or computing devices for any suitable reason. For instance, the eyewear may broadcast the identity of the wearer to a laptop computer for the wearer to gain access to the laptop computer without having to manually enter a password.

In various embodiments, the step of broadcasting the identity of the wearer to the one or more individuals or computing devices may also include translating the identity of the wearer into a picture, a name, an ID number, a password, a passcode, an access code, etc. For example, in the course of broadcasting the identity of the wearer to the computing device, the eyewear may first translate the identity of the wearer into a password associated with the wearer for one or more applications on the computing device, and then broadcast the password in any suitable manner. As a further example, in broadcasting the identity of the wearer to an individual such as the wearer's employer, the eyewear may translate the identity of the wearer into a unique image, such as a picture of the wearer.

Structure of the Eyewear

Figure 4:
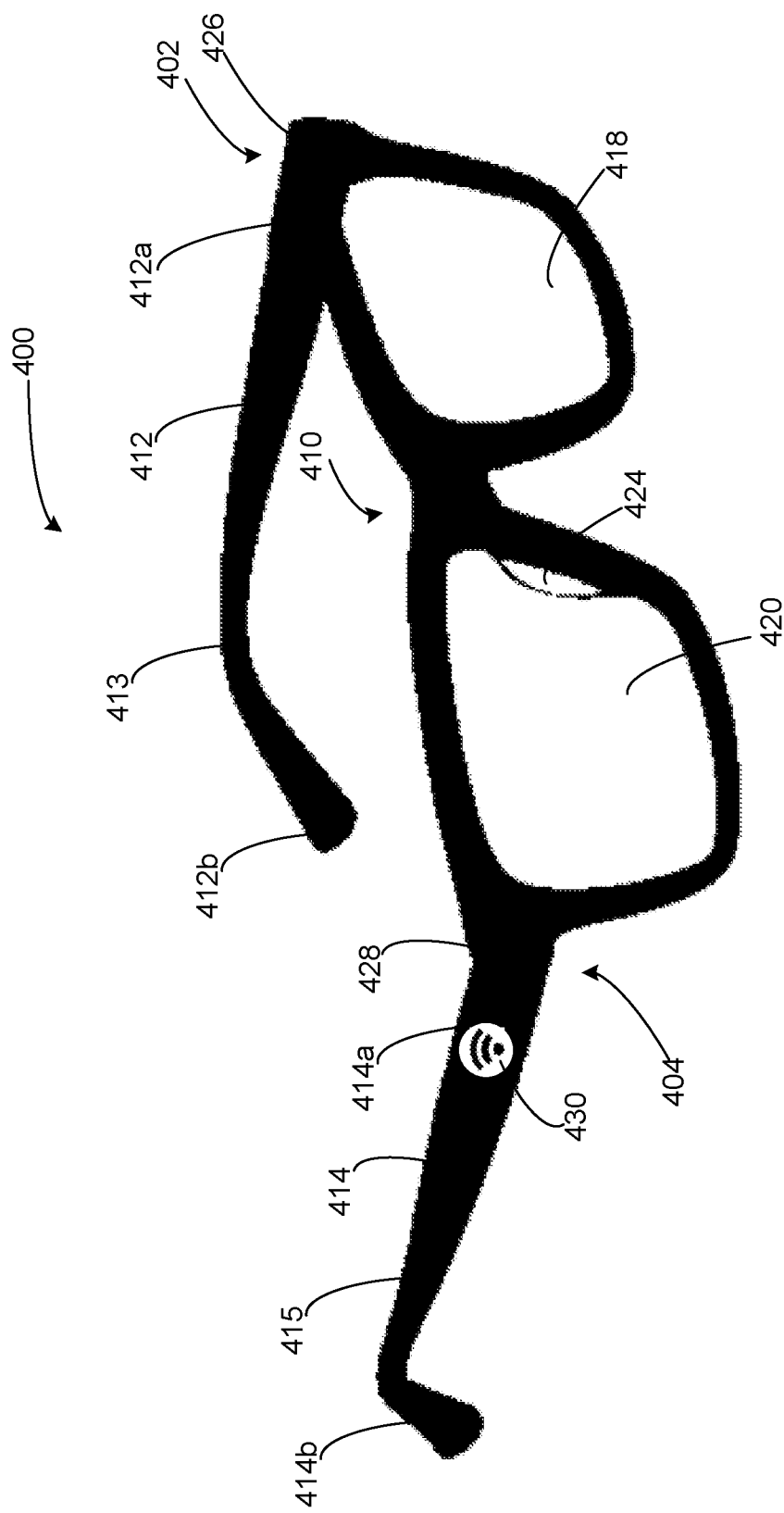
FIG. 4 is an exemplary wearable health monitoring device of FIG. 1.

As shown in FIG. 4, eyewear 400, according to various embodiments, includes: (1) an eyewear frame 410; (2) a first temple 412; and (3) a second temple 414. These various components are discussed in more detail below.

Eyewear Frame

Referring still to FIG. 4, the eyewear 400, in various embodiments, may include any suitable eyewear frame 410 configured to support one or more lenses 418, 420. In the embodiment shown in this figure, the eyewear frame 410 has a first end 402 and a second end 404. The eyewear frame 410 may be made of any suitable material such as metal, ceramic, one or more polymers or any combination thereof. In particular embodiments, the eyewear frame 410 is configured to support the first and second lenses 418, 420 about the full perimeter of the first and second lenses 418, 420. In other embodiments, the eyewear frame 410 may be configured to support the first and second lenses 418, 420 about only a portion of each respective lens. In various embodiments, the eyewear frame 410 is configured to support a number of lenses other than two lenses (e.g., a single lens, a plurality of lenses, etc.). In particular embodiments, the lenses 418, 420 may include prescription lenses, sunglass lenses, or any other suitable type of lens (e.g., reading lenses, non-prescription lenses), which may be formed from glass or one or more polymers.

The eyewear frame 410 includes a first and second nose pad 422 (not shown in figure), 424, which may be configured to maintain the eyewear 400 adjacent the front of a wearer's face such that the lenses 418, 420 are positioned substantially in front of the wearer's eyes while the wearer is wearing the eyewear 400. In particular embodiments, the nose pads 422, 424 may comprise a material that is configured to be comfortable when worn by the wearer (e.g., rubber, etc.). In other embodiments, the nose pads 422, 424 may include any other suitable material (e.g., plastic, metal, etc.). In still other embodiments, the nose pads 422, 424 may be integrally formed with the frame 410.

The eyewear frame 410 includes a first and second hinge 426, 428 that attach the first and second temples 412, 414 to the frame first and second ends 402, 404, respectively. In various embodiments, the hinges 426, 428 may be formed by any suitable connection (e.g., tongue and groove, ball and socket, spring hinge, etc.). In particular embodiments, the first hinge 426 may be welded to, or integrally formed with, the frame 410 and the first temple 412 and the second hinge 428 may be welded to, or integrally formed with, the frame 410 and the second temple 414.

First and Second Temples

As shown in FIG. 4, the first temple 412, according to various embodiments, is rotatably connected to the frame 410 at a right angle to extend the first temple 412 substantially perpendicular, substantially parallel, or anywhere in between the right angle to the frame 410. The first temple 412 has a first and second end 412a, 412b. Proximate the first temple second end 412b, the first temple 412 includes an earpiece 413 configured to be supported by a wearer's ear. Similarly, the second temple 414, according to various embodiments, is rotatably connected to the frame 410 at a right angle to extend the second temple 414 substantially perpendicular, substantially parallel, or anywhere in between the right angle to the frame 410. The second temple 414 has a first and second end 414a, 414b. Proximate the second temple second end 414b, the second temple 414 includes an earpiece 415 configured to be supported by a wearer's ear.

Sensors

In various embodiments, the second temple 414 has one or more sensors 430 connected to the second temple 414. In various embodiments, the one or more sensors 430 may be coupled to the frame 410, the first and second temples 412, 414, the first and second lenses 418, 410, or any other portion of the eyewear 400 in any suitable way. For instance, the one or more sensors 430 may be embedded into the eyewear 400, coupled to the eyewear 400, and/or operatively coupled to the eyewear 400. In various embodiments, the one or more sensors may be formed at any point along the eyewear 400. For instance, a fingerprint reader may be disposed adjacent the first temple of the eyewear 400. In various embodiments, the one or more sensors may be formed in any shape. In addition, the one or more sensors may be formed on the inner (back) surface of the frame 410, the first and second temples 412, 414, the first and second lenses 418, 410, or any other portion of the eyewear 400. In other embodiments, the one or more sensors may be formed on the outer (front) surface of the frame 410, the first and second temples 412, 414, the first and second lenses 418, 410, or any other portion of the eyewear 400.

In various embodiments, the one or more sensors 430 that are coupled to the eyewear (or other wearable device) are adapted to detect one or more characteristics of the eyewear or a wearer of the eyewear, wherein the one or more characteristics of the wearer are associated with the wearer's identity. In various embodiments, the one or more sensors coupled to the eyewear or other health monitoring device may include, for example, one or more of the following: a near-field communication sensor, a Bluetooth chip, a GPS unit, an RFID tag (passive or active), a fingerprint reader, an iris reader, a retinal scanner, a voice recognition sensor, a heart rate monitor, an electrocardiogram (EKG), a pedometer, a thermometer, a front-facing camera, an eye-facing camera, a microphone, an accelerometer, a magnetometer, a blood pressure sensor, a pulse oximeter, a skin conductance response sensor, any suitable biometric reader, or any other suitable sensor. In some embodiments, the one or more sensors may include a unique shape, a unique code, or a unique design physically inscribed into the eyewear that may be readable by an individual or a remote computing device. In particular embodiments, the sensors coupled to the eyewear may include one or more electronic communications devices such as a near field communication chip, a Bluetooth chip, an active RFID, and a GPS unit.

In various embodiments, the one or more sensors are coupled to a computing device that is associated with (e.g., embedded within, attached to) the eyewear or other wearable device. In particular embodiments, the eyewear or other wearable device comprises at least one processor, computer memory, suitable wireless communications components (e.g., a Bluetooth chip) and a power supply for powering the wearable device and/or the various sensors.

As noted above, the one or more sensors may be coupled to a Bluetooth device (e.g., a Bluetooth communications chip), or other wireless communications device, that is configured to transmit the one or more signals to a handheld wireless device, and the step of using the eyewear to confirm the identity of the wearer of the eyewear (discussed above in reference to Step 310) further comprises receiving the one or more signals from the wireless handheld device (e.g., via the Internet). In particular embodiments, one or more of the sensors may be detachable from the eyewear. For instance, if a wearer does not need a temperature sensor or other particular sensor, the sensor may be removed from the eyewear.

Functionality of the Eyewear

In various embodiments, different embodiments of the eyewear may identify the wearer in any suitable way. In particular embodiments, the eyewear may identify the wearer by broadcasting the identity of the wearer (e.g., always, at a particular time of day, in response to receiving a request, etc.). In some embodiments, the eyewear may broadcast the identity of the wearer by communicating a unique identifier to one or more individuals or computing devices without independently confirming the wearer's identity. For example, rather than confirming the identity of the wearer before notifying the individual of the wearer's identity, the eyewear may interpret possession of the eyewear to mean that the wearer is the owner of the eyewear or has permission from the owner of the eyewear to use their identity to perform one or more various activities (such as accessing a computer or a secure area). In various embodiments, in broadcasting the wearer's identity, the eyewear may transmit the wearer's identity substantially continuously. In certain embodiments, the eyewear may transmit the wearer's identity at least partially in response to receiving a request from a remote computing device for the wearer's identity. In still other embodiments, the eyewear may transmit the wearer's identity at least partially in response to receiving a "transmit identification" request from the wearer of the eyewear.

In particular embodiments, in transmitting the identification of the wearer, the eyewear may display a unique identifier on the outside of the eyewear. For example, the eyewear may capture the wearer's image and then the eyewear may display an OCR readable code, or other machine-readable code, that is associated with the wearer's identity. In other embodiments, in transmitting the identification of the wearer, the eyewear may have a unique shape such that the shape of the eyewear is a unique identifier. In still other embodiments, the unique shape of the eyewear in conjunction with the shape of the wearer's face may function as a unique identifier. For example, the eyewear may use facial recognition and/or object recognition techniques to determine the shape of the eyewear and the shape of the wearer's face.

In other embodiments, the eyewear may identify the wearer by first confirming the wearer's identity as the owner of the eyewear and then communicating the identity of the wearer (e.g., in any of the ways discussed above).

Exemplary User Experience

As discussed above, in various embodiments, the eyewear is adapted to confirm the identity of the wearer for any suitable reason. In particular embodiments, the eyewear may be used to interact (e.g., substantially automatically, or in response to an activation by one or more individuals or computing devices) with an adjacent computing device (or other computing device) to automatically confirm the identity of the individual. Several examples exist to demonstrate the eyewear confirming the identity of a wearer.

Identification for Access to a Computer

In a particular example, the eyewear may be used to confirm the identity of a wearer who wishes to access a computerized device (e.g., a handheld device), a computer program, or a particular electronic document on a computing device in order to accomplish a task, thereby eliminating the need for the wearer to manually enter a password. Before the wearer may gain access to the computerized device using the eyewear, the wearer may create an identity with the eyewear that will be used to access the computerized device. For instance, the wearer may place the eyewear on the wearer's face and request that the eyewear scan the wearer's face, eyes, fingerprint, and/or other attributes to determine the wearer's identity. The wearer may then create an account on the computerized device and instruct the computerized device to accept the wearer's identity from the eyewear as the wearer's password rather than requiring the wearer to manually enter a password into the computerized device. After setting up the computerized device to accept the wearer's identity from the eyewear, while the wearer is wearing the eyewear, the eyewear may confirm the identity of the wearer thereby eliminating the need for the wearer to enter a password to gain access to the computerized device.

Continuous Broadcasting of Identity

Similar to the wearer using the eyewear to access a computer, the eyewear may also continuously or intermittently broadcast the wearer's identity to access any computing device or application that requires a password or other authorizing information. For example, after creating an identity with the eyewear as described above, the wearer may enable various computing devices and applications to recognize the wearer's identity from the eyewear in lieu of entering a password to access the particular computer or computer program. Once the wearer has created an identity, the eyewear may continuously confirm the identity of the wearer by performing a retinal scan or any other suitable scan of the wearer. The eyewear will also continuously broadcast the wearer's identity at least partially in response to confirming the wearer's identity. This may allow the wearer to access particular computing devices, computer programs, restricted-access physical locations, etc. . . . by using a unique code sent from the eyewear to a suitable computing device without requiring the wearer to manually enter login information such as a username and password. For example, the wearer may walk into a room where the wearer's laptop computer and mobile phone are located. Although both of these devices require a password to unlock the devices, by walking within range of the devices with the eyewear on and wirelessly broadcasting the wearer's identity, both devices will unlock, thereby providing convenient access to the wearer without the wearer first entering an alphanumeric password.

In particular embodiments, the eyewear will cease broadcasting the wearer's identity at least partially in response to the eyewear determining that the wearer's identity can no longer be confirmed as that of a particular individual who is associated with the eyewear (e.g., the owner of the eyewear). For instance, where the wearer has removed the eyewear, the eyewear may stop broadcasting the wearer's identity as soon as the eyewear is unable to confirm the identity of the wearer due to the increased distance between the eyewear and the wearer. Also, in various embodiments, where the eyewear is worn by someone other than the owner of the eyewear, the eyewear will not be able to confirm the wearer's identity as the owner of the eyewear and may, accordingly, turn off the broadcasting of the wearer's identity. In such an embodiment, the eyewear may, in response to not being able to confirm the identity of the individual wearing the eyewear as the owner of the eyewear, send a notification to the owner of the eyewear (e.g., the wearer) that the eyewear is being worn by someone other than the wearer. In various embodiments, the eyewear may also capture the identity of the current wearer of the eyewear (e.g., an individual who has stolen the eyewear) using any suitable sensor (e.g., a face-facing camera) in order to alert a suitable individual of the identity of the individual who is currently in possession of the eyewear.

In various embodiments, the eyewear may also capture the identity of an individual who is determined not to be the owner of the eyewear in order to create a separate account for that individual so that each wearer of the eyewear has a unique identification established with the eyewear in order to access particular computing devices or applications. This may be particular suitable for non-prescription eyewear, such as sunglasses and vanity glasses.

Identification for Access to a Particular Area

In addition, the eyewear may be used to confirm the identity of a wearer who wishes to gain access to a secure area. For example, a secure area such as a passenger area of an airport or a secure area of a building may require identification to enter that particular area. In various embodiments, by wearing the eyewear, the wearer may be able to forgo the process of presenting a security badge or other identification to enter the particular area because the eyewear will confirm the identity of the wearer automatically. For example, in a building that requires a security badge to be swiped and a passcode to be entered in order to gain access to a particular area, the eyewear may be used to provide substantially instant access to the area by capturing an image of the wearer's face using the eye-facing camera and a fingerprint of the wearer using the fingerprint reader as the wearer enters an area with a computing device that communicates directly (e.g., wirelessly) with the eyewear. After receiving the image of the wearer and the wearer's fingerprint, the eyewear may confirm the identity of the wearer to the computing device, which may provide the wearer access to the secured area (e.g., by unlocking a door to the secured area, or by displaying an indication to a security guard that the individual should be allowed to enter the area).

Identification for Making a Payment

The situation may also arise where the eyewear confirms the identity of the wearer who wishes to make a payment for a particular good or service. In various embodiments, wearing the eyewear may eliminate the need for the wearer to confirm the wearer's identity before sending a wire, paying by credit or debit card, or paying by NFC (e.g., near field communication via the wearer's phone). Accordingly, in various embodiments, the eyewear may include wireless payment functionality. For example, the wearer may have his or her credit card information associated with the wearer's identity stored in the eyewear, or in a remote computing device associated with the eyewear. In the course of making a purchase at a retail location that accepts payment by wireless communications, in lieu of having payment completed via a swipe of the wearer's credit card, the eyewear may confirm the wearer's identity and then wirelessly communicate the wearer's credit card information to the retailer's payment terminal for use in facilitating payment for a particular item or service.

Identification for Signing a Document

In various embodiments, the eyewear may confirm the identity of a wearer signing a particular document. For instance, in signing an important legal document, the eyewear may confirm the identity of the wearer (e.g., in any suitable manner described above) in order to reduce the risk of fraud, etc. The eyewear may also be used to confirm a wearer's identity when no witnesses are available to confirm the wearer's identity. The eyewear, in this situation, may use one or more secure measurements such as a retinal scan, a fingerprint, etc. in order to confirm the identity of the wearer.

Conclusion

Many modifications and other embodiments of the invention will come to mind to one skilled in the art to which this invention pertains, having the benefit of the teaching presented in the foregoing descriptions and the associated drawings. For example, while various embodiments above describe certain processes (e.g., confirming the identity of an individual) as being done by a computing device associated with eyewear, in various embodiments, those processes may be done by a computer that is remote from the eyewear. For example, the eyewear may transmit a fingerprint pattern or other biometric information to a remote server, which would confirm the wearer's identity by matching the biometric information to biometric information for the owner of the eyewear that is stored in a database on the remote server. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for the purposes of limitation.

What is claimed is:

1. A computer-implemented method of providing a particular individual with access to a computer system or computer program, the method comprising:
    receiving at least one wireless signal from a wearable device, the at least one wireless signal comprising a unique identifier associated with the particular individual;
    at least partially in response to receiving the at least one wireless signal, comparing the unique identifier with a stored identifier for the particular individual; and
    at least partially in response to determining that the unique identifier at least partially matches the stored identifier, providing the particular individual with access to the computer system or computer program.

2. The computer-implemented method of claim 1, wherein the method further comprises:
    transmitting at least one wireless signal to the wearable device requesting an identification signal from the wearable device, wherein receiving the at least one wireless signal from the wearable device is completed after transmitting the at least one wireless signal to the wearable device.

3. The computer-implemented method of claim 1, further comprising providing the wearable device, the wearable device comprising:
    one or more processors;
    one or more sensors operatively coupled to the one or more sensors; and
    one or more wireless chips operatively coupled to the one or more processors, wherein the one or more sensors are configured to:
    generate a signal that confirms the identity of the particular individual; and
    the one or more wireless chips are configured to transmit the at least one wireless signal that comprises the unique identifier associated with the particular individual.

4. The computer-implemented method of claim 3, wherein the one or more sensors is a biometric sensor that is configured to identify the particular individual by an attribute selected from a group consisting of:
    the particular individual's finger print;
    the particular individual's voice;
    the particular individual's gait;
    the particular individual's one or more facial characteristics;
    the particular individual's iris;
    the particular individual's tear;
    the particular individual's blood; and
    the particular individual's DNA.

5. The computer-implemented method of claim 3, further comprising:
    determining a biometric reading of the particular individual from the generated signal;
    comparing the biometric reading of the particular individual with biometric data that is associated with the particular individual; and
    at least partially in response to the results of the biometric reading at least partially matching the biometric data associated with the particular individual, generating the unique identifier associated with the particular individual.

6. The computer-implemented method of claim 1, wherein the unique identifier is a passcode associated with the particular individual, and wherein the computer system or computer program is selected from a group consisting of:
    a secure entry system;
    a password protected computing device;
    a password protected smart phone;
    a password protected alarm system;
    an electronic payment system; and
    an automobile.

7. The computer-implemented method of claim 1, wherein providing the particular individual with access to the computer system or computer program comprises deactivating a home alarm system at least partially based on the unique identifier.

8. The computer-implemented method of claim 1, wherein providing the particular individual with access to the computer system or computer program comprises executing an electronic payment for the particular individual at least partially based on the unique identifier.

9. The computer-implemented method of claim 1, wherein providing the particular individual with access to the computer system or computer program comprises unlocking an automobile associated with the particular individual at least partially based on the unique identifier.

10. The computer-implemented method of claim 1, wherein the wearable device is selected from a group consisting of:
one or more contact lenses;
a wristwatch;
at least a portion of a shirt;
at least a portion of a pair of pants;
at least a portion of an undergarment;
at least a portion of a shirt;
at least a portion of a compression sleeve;
at least a portion of footwear;
at least a portion of a hat;
at least a portion of a helmet;
at least a portion of an orthopedic cast;
an adhesive bandage; and
a piece of jewelry.

11. A system for confirming an identity of an individual, the system comprising:
a wearable device comprising:
one or more processors;
one or more sensors operatively coupled to the one or more processors; and
at least one electronic communications device operatively coupled to the one or more processors and adapted to broadcast a wireless signal comprising a unique identifier associated with a particular individual wearing the wearable device,
wherein the wireless signal is configured to be received by a remote computer system that uses the unique identifier to compare to a stored identifier for the particular individual so that the remote computer system can allow the particular individual access to one of the remote computer system, a secure area associated with the remote computer system, or a payment system associated with the remote computer system.

12. The system of claim 11, wherein the wearable device is selected from a group consisting of:
one or more contact lenses;
a wristwatch;
at least a portion of a shirt;
at least a portion of a pair of pants;
at least a portion of an undergarment;
at least a portion of a shirt;
at least a portion of a compression sleeve;
at least a portion of footwear;
at least a portion of a hat;
at least a portion of a helmet;
at least a portion of an orthopedic cast;
an adhesive bandage; and
a piece of jewelry.

13. The system of claim 12, wherein the one or more sensors comprises a biometric sensor configured to capture biometric information from the particular individual, the biometric information selected from a group consisting of:
the particular individual's finger print,
the particular individual's voice,
the particular individual's one or more facial characteristics,
the particular individual's iris,
the particular individual's tear,
the particular individual's blood, and
the particular individual's DNA; and
the one or more processors analyze the captured information from the biometric sensor and generate the unique identifier.

14. The system of claim 12, wherein:
the biometric sensor captures information about the particular individual's gait; and
the one or more processors analyze the particular individuals gait information and generate the unique identifier based on the analyzed gait information.

15. The system of claim 11, further comprising a remote computer system comprising:
one or more processors;
memory operatively coupled to the one or more processors; and
one or more electronic communication devices that is operatively coupled to the one or more processors of the remote computer system, wherein the remote computer system is configured to:
receive the wireless signal from the wearable device containing the unique identifier associated with the particular individual;
at least partially in response to receiving the wireless signal, compare the unique identifier with a stored identifier for the particular individual; and
at least partially in response to determining that the unique identifier at least partially matches the stored identifier, allow the particular individual access to one of the remote computer system, a secure area associated with the remote computer system, or a payment system associated with the remote computer system.

16. The system of claim 15, wherein the remote computer system is associated with an automobile and the remote computer system allows the particular individual to access the automobile when the unique identifier at least partially matches the stored identifier.

17. The system of claim 15, wherein the remote computer system is associated with a smartphone and the remote computer system allows the particular individual access to the smartphone when the unique identifier at least partially matches the stored identifier.

18. A system for confirming an identity of an individual, the system comprising:
a wearable device comprising:
one or more processors operative to receive a unique identifier associated with the individual from one or more sensors; and
one or more electronic communication devices operatively coupled to the one or more processors and configured to broadcast a wireless signal comprising the unique identifier associated with the individual wearing the wearable device,
wherein the wireless signal is configured to be received by a remote computer system that uses the unique identifier to compare to a stored identifier for the individual so that the remote computer system can allow the individual access to one of the remote computer system, a secure area associated with the remote computer system, or a payment system associated with the remote computer system.

19. The system of claim 18, further comprising the remote computer system comprising:
one or more processors;
memory operatively coupled to the one or more processors; and
one or more electronic communication devices that is operatively coupled to the one or more processors of the remote computer system,
wherein the remote computer system is configured to:
receive the wireless signal from the computerized eyewear containing the unique identifier associated with the individual;

at least partially in response to receiving the wireless signal, compare the unique identifier with a stored identifier for the individual; and at least partially in response to determining that the unique identifier at least partially matches the stored identifier, allow the individual access to one of the remote computer system, the secure area associated with the remote computer system, or the payment system associated with the remote computer system.

20. The system of claim 18, wherein the wearable device is selected from a group consisting of:
one or more contact lenses;
a wristwatch;
at least a portion of a shirt;
at least a portion of a pair of pants;
at least a portion of an undergarment;
at least a portion of a shirt;
at least a portion of a compression sleeve;
at least a portion of footwear;
at least a portion of a hat;
at least a portion of a helmet;
at least a portion of an orthopedic cast;
an adhesive bandage; and
a piece of jewelry.

* * * * *